US012564721B2

(12) United States Patent
Bonner et al.

(10) Patent No.: US 12,564,721 B2
(45) Date of Patent: Mar. 3, 2026

(54) ASSESSING PACEMAKER DEPENDENCY

(71) Applicant: Medtronic, Inc., Minneapolis, MN (US)

(72) Inventors: Matthew D. Bonner, Plymouth, MN (US); Robert D. Musto, Champlain, MN (US); Wade M. Demmer, Coon Rapids, MN (US); Todd J. Sheldon, North Oaks, MN (US); Michelle M. Galarneau, Eagan, MN (US); Vinod Sharma, Maple Grove, MN (US); Maureen E. Lybarger, New Brighton, MN (US); Greggory R. Herr, Blaine, MN (US); Alyssa L. Paul, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 772 days.

(21) Appl. No.: 17/655,800

(22) Filed: Mar. 22, 2022

(65) Prior Publication Data

US 2022/0314006 A1     Oct. 6, 2022

Related U.S. Application Data

(60) Provisional application No. 63/170,686, filed on Apr. 5, 2021.

(51) Int. Cl.
*A61N 1/37*     (2006.01)
*A61N 1/365*     (2006.01)
*A61N 1/372*     (2006.01)

(52) U.S. Cl.
CPC ....... *A61N 1/3706* (2013.01); *A61N 1/36592* (2013.01); *A61N 1/37223* (2013.01); *A61N 1/37247* (2013.01)

(58) Field of Classification Search
CPC ........................ A61N 1/3706; A61N 1/37247
See application file for complete search history.

(56) References Cited

U.S. PATENT DOCUMENTS 5,697,959 A     12/1997 Poore
6,584,352 B2     6/2003 Combs et al.
(Continued)

FOREIGN PATENT DOCUMENTS

WO     2013/096407 C     6/2013

OTHER PUBLICATIONS

International Search Report and Written Opinion of International Application No. PCT/US2022/021453, dated Jun. 22, 2022, 11 pp.
(Continued)

*Primary Examiner* — George R Evanisko
(74) *Attorney, Agent, or Firm* — Shumaker & Sieffert, P.A.

(57) ABSTRACT

A system includes an implantable medical device (IMD) and processing circuitry. The IMD includes sensing circuitry configured to sense cardiac electrical signals of a patient, and therapy delivery circuitry configured to deliver demand cardiac pacing to a heart of the patient based on the cardiac electrical signals. The processing circuitry is configured to: determine, for each of a plurality of time units, based on the cardiac electrical signals and the delivery of demand cardiac pacing during the time units, a plurality of metrics indicative of a need for continued delivery of demand cardiac pacing to the heart of the patient. The plurality of metrics includes a metric associated with a duration of one or more pacing episodes during the time unit. The processing circuitry is further configured to generate a graphical representation of the plurality of metrics of the plurality of time units for presentation to a user.

24 Claims, 9 Drawing Sheets

(56)                    References Cited

U.S. PATENT DOCUMENTS

| | | | |
|---|---|---|---|
| 6,907,287 | B1 | 6/2005 | Bevan et al. |
| 7,058,443 | B2 | 6/2006 | Struble |
| 7,627,374 | B1 | 12/2009 | Farazi et al. |
| 8,346,369 | B2 | 1/2013 | Mahajan et al. |
| 8,983,603 | B2 | 3/2015 | Perschbacher et al. |
| 9,724,519 | B2 | 8/2017 | Demmer et al. |
| 10,441,798 | B2 | 10/2019 | Yoon et al. |
| 10,632,313 | B2 | 4/2020 | Juffer et al. |
| 2005/0137629 | A1* | 6/2005 | Dyjach .................... A61N 1/37 607/9 |
| 2011/0040346 | A1 | 2/2011 | Sheldon |
| 2017/0296835 | A1 | 10/2017 | Yoon et al. |
| 2018/0361162 | A1 | 12/2018 | Ternes et al. |
| 2019/0083789 | A1 | 3/2019 | Thakur et al. |
| 2019/0168007 | A1 | 6/2019 | Stahmann et al. |
| 2019/0168008 | A1 | 6/2019 | Maile et al. |
| 2019/0374781 | A1 | 12/2019 | Stadler et al. |
| 2020/0009380 | A1 | 1/2020 | Casavant et al. |
| 2020/0121187 | A1 | 4/2020 | Sarkar et al. |

OTHER PUBLICATIONS

Communication pursuant to Article 94(3) EPC from counterpart European Application No. 22715905.0 dated Dec. 4, 2025, 4 pp.

* cited by examiner

DELIVER DEMAND CARDIAC PACING TO A HEART OF A PATIENT ⟋402

DETERMINE, FOR EACH OF A PLURALITY OF TIME UNITS, A PLURALITY OF METRICS INDICATIVE OF A NEED FOR CONTINUED DELIVERY OF DEMAND CARDIAC PACING ⟋404

GENERATE A GRAPHICAL REPRESENTATION OF THE PLURALITY OF METRICS OF THE PLURALITY OF TIME UNITS FOR PRESENTATION TO A USER ⟋406

DELIVER DEMAND CARDIAC PACING USING A
TARGET PACING INTERVAL ⟋602

CRITERIA FOR ENTERING
STEP-DOWN MODE SATISFIED? ⟋604

NO

YES

STEP-DOWN DEMAND PACING RATE ⟋606

CRITERIA FOR EXITING
STEP-DOWN MODE SATISFIED? ⟋608

NO

YES

STORE METRIC DATA FOR STEP-DOWN MODE ⟋610

800A

800B

| Since 05-Nov-2019 | | |
|---|---|---|
| Data: Pacing Episodes | | |
| Episodes Detected Total time in Episodes: 401500 mins | | |
| Date | Start Time | Duration (hh:mm:ss) |
| 12-Nov-19 | 3:22 | 14:07:03 |
| 12-Nov-19 | 17:30 | 13:10:45 |
| 13-Nov-19 | 6:42 | 11:11:11 |
| 13-Nov-19 | 17:54 | 7:11:21 |
| 14-Nov-19 | 1:20 | 0:45:56 |
| 14-Nov-19 | 3:50 | 0:12:23 |
| 15-Nov-19 | 1:25 | 0:09:04 |

ASSESSING PACEMAKER DEPENDENCY

This application claims the benefit of U.S. Provisional Application Ser. No. 63/170,686, filed Apr. 5, 2021, the entire content of which is incorporated herein by reference.

TECHNICAL FIELD

The disclosure relates to medical devices and, more particularly, medical devices for monitoring or assessing heart conditions and delivering cardiac pacing.

BACKGROUND

A variety of medical devices have been used or proposed for use to deliver therapy and/or monitor the physiological condition of patients. As examples, such medical devices may deliver therapy and/or monitor conditions associated with the heart, muscle, nerve, brain, stomach, or other organs or tissue. Medical devices that deliver therapy include medical devices that deliver one or both of electrical stimulation or a therapeutic agent to the patient.

An implantable pacemaker may monitor conditions of the patient's heart and may deliver pacing pulses to a patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle of the patient's heart) such that electrodes at the distal ends of the electrical leads are positioned at a target site. The pulse generator may provide electrical stimulation to the target site via the electrodes.

In some situations, someone who initially requires cardiac pacing may no longer need cardiac pacing. In some situations, the need for cardiac pacing may be anticipated to be temporary at the time of pacemaker implant. For example, a patient may need cardiac pacing after a cardiac procedure, such as a heart valve replacement or other heart surgery, and the need for pacing may be temporary. Unnecessary electrical stimulation may lead to one or more disadvantages, such as detrimental effects on cardiac structure and function, complications associated with device infection (e.g., including skin erosion at the pacemaker implant site), and the inconvenience of periodic follow up office visits.

SUMMARY

This disclosure describes techniques for assessing pacemaker dependency after pacemaker implantation. Processing circuitry of a medical device system that includes an implantable medical device (IMD) that delivers cardiac pacing may be configured to determine a plurality of metrics of a time unit, where the plurality of metrics indicative of a need for continued delivery of demand cardiac pacing to a heart of a patient by the IMD. The processing circuitry may determine the plurality of metrics of the time unit based on cardiac electrical signals acquired by the IMD during the time unit and the delivery of demand cardiac pacing from the IMD during the time unit. In some examples, the processing circuitry may determine a plurality of metrics of a plurality of time units. The processing circuitry may further generate a graphical representation of the plurality of metrics of the plurality of time units for presentation to a user (e.g., a physician). As used herein, a graphical representation may include any visual representation, such as graphs or tables.

In some examples, the plurality of metrics of the time unit may include a first metric that is associated with a duration of one or more pacing episodes during the time unit, where each of the one or more pacing episodes includes a respective plurality of consecutive cardiac cycles during which the demand cardiac pacing was delivered for at least a threshold portion of the cardiac cycles. In some examples, the plurality of metrics of the time unit may include a second metric that is associated with an amount of the demand cardiac pacing delivered during the time unit. In some examples, the plurality of metrics of the time unit may further include a third metric that is associated with a heart rate of the patient during the time unit. In some examples, the plurality of metrics may comprise a metric comprising a diagnostic mode event log. Example diagnostic modes include a suspend mode or a step-down mode.

In some examples, the IMD may be configured to operate in a suspend mode. In the suspend mode, the IMD is configured to deliver the demand cardiac pacing using a target pacing interval, suspend the demand cardiac pacing for a time period, and resume the demand cardiac pacing using the target pacing interval. The processing circuitry may be configured to determine at least one of the plurality of metrics based on data collected by the IMD during the time period, and the IMD may resume the demand cardiac pacing using the target pacing interval based on the collected at least one of the plurality of metrics.

Additionally, the IMD may be configured to operate in a step-down mode. In the step-down mode, the IMD is configured to deliver the demand cardiac pacing using a target pacing interval, deliver step-down cardiac pacing using a step-down pacing interval for a time period, and resume the demand cardiac pacing using the target pacing interval. The processing circuitry may be configured to determine at least one of the plurality of metrics based on data collected by the IMD during the time period, and the IMD may resume the demand cardiac pacing using the target pacing interval based on the collected at least one of the plurality of metrics. In some examples, the plurality of metrics may comprise a metric associated with a length of the time period, e.g., in which the IMD was able to operate in a diagnostic mode, such as the suspend or step-down mode.

The techniques of this disclosure may provide one or more advantages. For example, the operation of the IMD and the metrics collected may allow a clinician to readily visualize a level of dependence of the patient on continued delivery of demand cardiac pacing. Traditional cardiac pacemakers do not assess continued dependency of cardiac pacing. The clinician may be able to more confidently determine whether to continue or discontinue temporary cardiac pacing and, if necessary, implant a permanent cardiac pacemaker.

In one example, the disclosure is directed to a system comprising: an implantable medical device (IMD) comprising: sensing circuitry configured to sense, via a plurality of electrodes, cardiac electrical signals of a patient; therapy delivery circuitry configured to deliver demand cardiac pacing to a heart of the patient via the plurality of electrodes based on the cardiac electrical signals; and processing circuitry configured to: determine, for each of a plurality of time units, based on the cardiac electrical signals and the delivery of demand cardiac pacing during the time units, a plurality of metrics indicative of a need for continued delivery of demand cardiac pacing to the heart of the patient, wherein the plurality of metrics comprise: a first metric, wherein the first metric is associated with a duration of one or more pacing episodes during the time unit, each of the one or more pacing episodes comprising a respective plurality of consecutive cardiac cycles during which the demand cardiac pacing was delivered for at least a threshold portion of the cardiac cycles; and generate a graphical representation of the plurality of metrics of the plurality of time units for presentation to a user.

In another example, the disclosure is directed to a method comprising: sensing, via a plurality of electrodes of an implantable medical device (IMD), cardiac electrical signals of a patient; delivering demand cardiac pacing to a heart of the patient via the plurality of electrodes based on the cardiac electrical signals; determining, for each of a plurality of time units, based on the cardiac electrical signals and the delivery of demand cardiac pacing during the time units, a plurality of metrics indicative of a need for continued delivery of demand cardiac pacing to the heart of the patient, wherein the plurality of metrics comprise: a first metric, wherein the first metric is associated with a duration of one or more pacing episodes during the time unit, each of the pacing episodes comprising a respective plurality of consecutive cardiac cycles during which the demand cardiac pacing was delivered for at least a threshold portion of the cardiac cycles; and generating a graphical representation of the plurality of metrics of the plurality of time units for presentation to a user.

In another example, the disclosure is directed to a non-transitory computer-readable storage medium comprising program instructions that, when executed by processing circuitry of a medical system, cause the processing circuitry to: sense, via a plurality of electrodes of an implantable medical device (IMD), cardiac electrical signals of a patient; deliver demand cardiac pacing to a heart of the patient via the plurality of electrodes based on the cardiac electrical signals; determine, for each of a plurality of time units, based on the cardiac electrical signals and the delivery of demand cardiac pacing during the time units, a plurality of metrics indicative of a need for continued delivery of demand cardiac pacing to the heart of the patient, wherein the plurality of metrics comprise: a first metric, wherein the first metric is associated with a duration of one or more pacing episodes during the time unit, each of the pacing episodes comprising a respective plurality of consecutive cardiac cycles during which the demand cardiac pacing was delivered for at least a threshold portion of the cardiac cycles; and generate a graphical representation of the plurality of metrics of the plurality of time units for presentation to a user.

The summary is intended to provide an overview of the subject matter described in this disclosure. It is not intended to provide an exclusive or exhaustive explanation of the systems, devices, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters refer to like elements throughout the figures and description.

DETAILED DESCRIPTION

Figure 1:
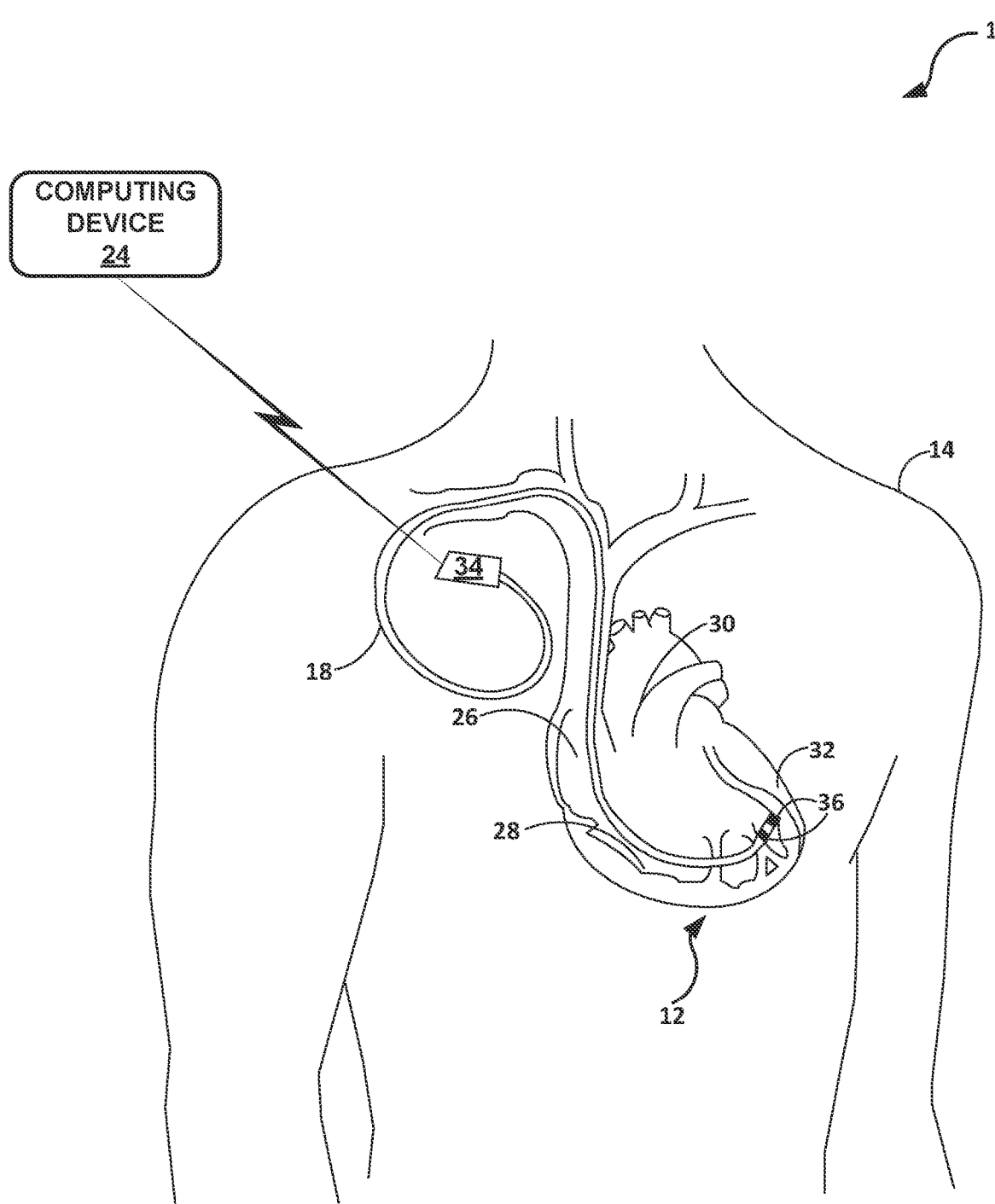
FIG. 1 is a diagram illustrating an example therapy system that may be used to monitor one or more physiological parameters of a patient and/or to provide therapy to the heart of the patient.

FIG. 1 is a diagram illustrating an example medical device system 10 that may be used to provide cardiac pacing therapy to the heart 12 of a patient 14 and to assess pacemaker dependency of patient 14. The example techniques may be used with an implantable medical device (IMD) 34, which is a cardiac pacemaker and may be in wireless communication with at least one of computing device 24 and other devices not pictured in FIG. 1. IMD 34 may be implanted outside of a thoracic cavity of patient 14 (e.g., pectoral location illustrated in FIG. 1). Although described in the context of examples in which the cardiac pacemaker is implanted or implantable, the techniques described herein may be used in system that additionally or alternatively include an external cardiac pacemaker.

In some examples, as illustrated in FIG. 1, IMD 34 is coupled to a lead 18. At some instances in this disclosure, IMD 34 and lead 18 may be referred to individually or collectively as an IMD. In some examples, IMD 34 may be an implantable pacemaker (e.g., a cardiac pacing device) that delivers electrical signals to heart 12 via electrodes coupled to lead 18. IMD 34 also senses electrical activity of heart 12 via the one or more electrodes of lead 18. Lead 18 may be electrically coupled to a sensing circuitry and therapy delivery circuitry of IMD 34. In some examples, a proximal end of lead 18 may include one or more electrical contacts that electrically couple to respective electrical contacts within a lead connector of IMD 34.

In the example illustrated by FIG. 1, lead 18 is a right ventricular (RV) lead that extends through one or more veins (not shown), the superior vena cava (not shown), right atrium 26, and into right ventricle 28. Lead 18 may deliver RV pacing to heart 12. In another example, lead 18 may be a left ventricular (LV) lead that extends through one or more veins, the vena cava, right atrium 26, and into the coronary sinus 30, to a region adjacent to the free wall of left ventricle 32 of heart 12. In such examples, lead 18 may deliver LV pacing to heart 12. In another example still, lead 18 is a right atrial (RA) lead that extends through one or more veins and the vena cava, and into the right atrium 26 of heart 12. In such examples, lead 18 may deliver RA pacing to heart 12. While shown in FIG. 1 as being implanted in the pectoral region of patient 14, it will be appreciated that, in other examples, IMD 34 may be implanted at other locations, such as in the neck or arm region of patient 14, etc. Also, while lead 18 is shown as extending into right ventricle 28 and delivering endocardial pacing, it will be appreciated that in other examples, lead 18 may contact other areas, such as other chambers of heart 12 or an epicardial region of patient 14.

IMD 34 of system 10 may sense electrical signals attendant to the depolarization and repolarization of heart 12 via one or more electrodes 36 coupled to lead 18. IMD 34 provides pacing pulses to heart 12 via electrodes 36 based on these sensed electrical signals. The configurations of electrodes used by IMD 34 for sensing and pacing may be unipolar or bipolar, depending on whether lead 18 is a unipolar lead or is a bipolar lead. In some examples, IMD 34 may include one or more electrodes on or formed by a housing of the IMD, which IMD 34 may use to sense cardiac signals and/or deliver cardiac pacing. Moreover, IMD 34 may additionally or alternatively include one or more other sensors, such as one or more optical sensors, accelerometers, temperature sensors, chemical sensors, light sensors, pressure sensors, in some examples. Such sensors may detect one or more physiological parameters indicative of the condition of a patient.

Although described primarily in the context of system 10, which includes IMD 34 and a single endocardial lead 18 configured for VVI pacing, the techniques of this disclosure may be implemented in other, differently configured medical device systems. In some examples, the techniques of this disclosure may be implemented in systems configured to sense atrial activity and deliver VDD cardiac pacing. In such systems, lead 18 or an additional lead may include electrodes for sensing electrical activity of the atrium, or lead 18, an additional lead, or IMD 24 may include one or more sensors for sensing mechanical activity of the atrium, such as one or more accelerometers. In addition to delivering VDD pacing based on the sensed atrial activity, such systems may collect atrioventricular conduction information, as described in greater detail below. Furthermore, in some examples, the techniques of this disclosure may be implemented in systems that include one or more "leadless" cardiac pacemakers, such as the Micra™ AV and VR pacemakers commercially available for Medtronic, plc, of Dublin, Ireland, implanted within or on the heart, instead or in addition to IMD 34 and lead 18. One or more leadless cardiac pacemakers may be configured to sense atrial activity and provide VDD pacing.

Computing device 24 may be used to communicate with IMD 34. For example, a user may use computing device 24 to retrieve information from IMD 34 regarding physiological parameters of patient 14, the delivery of cardiac pacing to patient 14, and the dependence of patient 14 on the delivery of cardiac pacing by IMD 34, and may interact with computing device 24 to program, e.g., select parameters for, therapies and sensing provided by IMD 34.

In some examples, computing device 24 may be a handheld computing device with a display viewable by the user and an interface for providing input to computing device 24 (i.e., a user input mechanism). For example, computing device 24 may include a small display screen (e.g., a liquid crystal display (LCD) or a light emitting diode (LED) display) that presents information to the user. In addition, computing device 24 may include a touch screen display, keypad, buttons, a peripheral pointing device, voice activation, or another input mechanism that allows the user to navigate through the user interface of computing device 24 and provide input. If computing device 24 includes buttons and a keypad, the buttons may be dedicated to performing a certain function, e.g., a power button, the buttons and the keypad may be soft keys that change in function depending upon the section of the user interface currently viewed by the user, or any combination thereof.

In some examples, IMD 34 may receive and store information about the level of detail of results of the pacemaker dependency assessment that patient 14 or a third party may receive, which may be determined by the manufacturer of IMD 34, patient 14, a third party, or some combination thereof. In some examples, patient 14 and the third party may receive results of the pacemaker dependency assessment with different levels of detail. In some examples, a user of computing device 24 may provide inputs about the level of detail of the results of the pacemaker dependency assessment speech the user would like to receive to computing device 24. For example, patient 14 may prefer to receive a conclusive result, whereas a care provider may prefer to receive for individual metrics.

In some examples, computing device 24 may be a larger workstation or a separate application within another multifunction device, rather than a dedicated computing device. For example, the multi-function device may be a notebook computer, tablet computer, workstation, one or more servers, cellular phone, personal digital assistant, or another computing device that may run an application that enables the computing device to operate as a secure device.

Computing device 24 may be configured to communicate with IMD 34 and, optionally, another computing device (not illustrated in FIG. 1), via wireless communication. Computing device 24, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies). In examples, computing device 24 may be a local device in wireless communication with IMD 34. In examples, computing device 24 may be a remotely located part of a networked computing system configured to communicate wirelessly with IMD 34. The computing system may include one or more remote servers and one or more user devices able to communicate with the servers via a network.

In accordance with the techniques of the disclosure, IMD 34 may detect cardiac electrical signals of patient 14 and monitor delivery of pacing to patient 14 for assessing pacemaker dependency after pacemaker implantation. IMD 34 may operate in one of a plurality of operating modes for detecting cardiac electrical signals of patient 14 and monitoring delivery of cardiac pacing to patient 14 for a plurality of time units, and processing circuitry of system 10, e.g., processing circuitry of IMD 34 and/or computing device 24, may determine and present a plurality of metrics indicative of a need for continued delivery of demand cardiac pacing to the heart of the patient based at least in part of the detected cardiac electrical signals and the delivery of pacing.

In some examples, the plurality of operating modes may include a normal mode, a suspend mode, and a step-down mode. The suspend mode and step-down mode may be examples of diagnostic modes configured to assess pacemaker dependency. As described above, IMD 34 may operate in one of the plurality of operating modes. Further, IMD 34 may be operable to switch between the plurality of modes. For example, a clinician may program IMD 34 to operate in one of the pluralities of operating modes, e.g., to determine metrics as described herein during an office visit. In some examples, IMD 34 may automatically select an operating mode. In some examples, IMD 34 may automatically switch from one operating mode to another operating mode, such as switching from a normal mode to a suspend mode or a step-down mode for a specified period of time. In some examples, IMD 34 may IMD 34 may automatically switch from one operating mode to another operating mode according to a schedule, pre-set pacing or sensing criteria, and/or other information programmed into IMD 34, e.g., by a user via computing device 24.

In some examples, the processing circuitry may determine, for each of a plurality of time units and based on the cardiac electrical signals and the delivery of demand cardiac pacing during the time units, a plurality of metrics indicative of a need for continued delivery of demand cardiac pacing to the heart of patient 14. The processing circuitry may further generate a graphical representation of the plurality of metrics of the plurality of time units for presentation to a user. In some examples, the graphical representation may be presented via computing device 24 in wireless communication with IMD 34.

In some examples, the plurality of metrics indicative of a need for continued delivery of demand cardiac pacing to the heart of patient 14 includes a metric that is associated with a duration of one or more pacing episodes during the time unit, where each of the one or more pacing episodes includes a respective plurality of consecutive cardiac cycles during which the demand cardiac pacing was delivered for at least a threshold portion of the cardiac cycles. In one example, the metric includes at least one of a number of the respective plurality of consecutive cardiac cycles, e.g., with an associated pacing rate, or total time duration of the episode for each of the one or more pacing episodes. The threshold portion of the consecutive cardiac cycles may be all of the consecutive cardiac cycles or a portion less than all of the consecutive cardiac cycles, such as all but a predetermined number or percentage of the consecutive cardiac cycles.

In some examples, the plurality of metrics indicative of a need for continued delivery of demand cardiac pacing to the heart of patient 14 includes a metric that is associated with an amount of the demand cardiac pacing delivered during the time unit.

In some examples, the plurality of metrics indicative of a need for continued delivery of demand cardiac pacing to the heart of patient 14 includes a metric that is associated with a heart rate of the patient during the time unit. For example, this metric may include any mid-based statistic, such as at least one of an average heart rate, a median heart rate, or a mode heart rate, an absolute minimum heart rate, a low-percentile heart rate (e.g., 5%), an absolute maximum heart rate, or a high-percentile heart rate (e.g., 95%) of patient 14 during the time unit.

In some examples, the plurality of metrics comprises a metric comprising a diagnostic mode event log. Furthermore, in some examples, the plurality of metrics comprises a metric associated with a length of the time period, e.g., during which the IMD was able to operate in a diagnostic mode before termination criteria were satisfied.

In some examples, IMD 34 may operate in a suspend mode, e.g., in which delivery of cardiac pacing is suspended, for a specified amount of time. The processing circuitry may determine, for each of a plurality of time units during the specified amount of time in which IMD 34 operates in the suspend mode and based on the cardiac electrical signals and the delivery of demand cardiac pacing during the time units, a plurality of metrics indicative of a need for continued delivery of demand cardiac pacing to the heart of patient 14. For example, when IMD 34 operates in a suspend mode, IMD 34 may deliver the demand cardiac pacing using a target pacing interval, e.g., an escape interval such as a V-V interval or A-V interval, suspend the demand cardiac pacing for a time period, and resume the demand cardiac pacing using the target pacing interval. In one example, the processing circuitry may determine at least one of the plurality of metrics during the time period, and IMD 34 may resume the demand cardiac pacing using the target pacing interval based on the collected at least one of the plurality of metrics. For example, if IMD 34 determines that the collected plurality of metrics are indicative of a need for continued delivery of demand cardiac pacing, IMD 34 may stop operating in the suspend mode (e.g., not completing the specified amount of time) and resume the demand cardiac pacing using the target pacing interval. If IMD 34 determines the collected plurality of metrics does not indicate a need for continued delivery of demand cardiac pacing, IMD 34 may continue to operate in the suspend mode for the specified amount of time.

In some examples, IMD 34 may operate in a step-down mode, e.g., in which the rate floor of demand cardiac pacing is lowered, for a specified amount of time. The processing circuitry may further determine, for each of a plurality of time units during the specified amount of time and based on the cardiac electrical signals and the delivery of demand cardiac pacing during the time units, a plurality of metrics indicative of a need for continued delivery of demand cardiac pacing to the heart of patient 14. For example, when IMD 34 operates in a step-down mode, IMD 34 may deliver the demand cardiac pacing using a target pacing interval, deliver step-down cardiac pacing using a step-down pacing interval for a time period, and resume the demand cardiac pacing using the target pacing interval. In one example, IMD 34 may collect at least one of the plurality of metrics during the time period, and may resume the demand cardiac pacing using the target pacing interval based on the collected at least one of the plurality of metrics. For example, if IMD 34 determines the collected plurality of metrics indicates a need for continued delivery of demand cardiac pacing, IMD 34 may stop operating in the step-down mode (e.g., not completing the specified amount of time) and resume the demand cardiac pacing using the target pacing interval. If IMD 34 determines the collected plurality of metrics does not indicate a need for continued delivery of demand cardiac pacing, IMD 34 may continue to operate in the step-down mode for the specified amount of time.

In examples in which IMD 34 is configured for atrial sensing, IMD 34 may collect atrioventricular conduction metrics indicative of the need for continued cardiac pacing. Example atrioventricular conduction metrics indicative of the need for continued cardiac pacing include a ratio of sensed atrial events to sensed ventricular events, intervals between sensed atrial events and sensed ventricular events, or variability of intervals between sensed atrial events and sensed ventricular events, e.g., sensed P-waves or atrial contractions and R-waves. If the ratio of atrial events to ventricular events is greater than 1 and the atrial events are appropriately timed (e.g., not premature atrial contractions), the patient may have second degree or higher atrioventricular block. If the patient has intervals between atrial and ventricular events longer than a threshold, the patient may have first degree atrioventricular block. If there is no consistent timing between atrial and ventricular events, the patient likely has third degree atrioventricular block.

When operating in diagnostic modes, IMD 34 may generate metrics indicative of when intrinsic heart rate drops falls below a low threshold based upon a dropped beat and/or a low escape rate, which may reflect a high-grade atrioventricular block. Such atrioventricular block may be evident in heart rate trend/histogram data, as well as the episode logs generated by processing circuitry according to the techniques descried herein. In addition, IMD 34 may store R-R interval strips surrounding pacing episodes. In cases of Wenckebach (second degree type I block), R-R intervals usually progressively shorten leading up to dropped beat. In cases of second degree type II block, R-R intervals are generally stable leading up to the dropped beat. A clinician can manually review these R-R strips to help them make a diagnosis of atrioventricular block.

R-R interval strips may include a number of intervals preceding and following an episode, such as a pacing episode, which may allow a clinician to distinguish different types of blocks or pauses. In some examples, R-R interval strips collected by an IMD 34 for pacing episodes may allow a clinician to distinguish vagally mediated pauses from more abrupt pauses due to atrioventricular block. IMD 34 may also store episode logs, e.g., R-R interval strips, for other episodes, such as high-rate episodes, which may provide context to a clinician for understanding high-rate episodes, and/or serve as a pseudo ventricular tachyarrhythmia detector.

In some examples, IMD 34 and/or computing device 24 may send the plurality of metrics and/or the graphical representation of the plurality of metrics of the plurality of time units to a monitoring center, such as via a wireless network connection and/or over the Internet, so that the monitoring center may analyze the plurality of metrics to create a report and/or present the graphical representation of the plurality of metrics of the plurality of time units for review by, for example, a clinician.

The techniques of the disclosure may provide specific improvements to the field of assessing pacemaker dependency after implantation of a pacemaker, such as IMD 34. For example, the techniques of the disclosure may enable medical devices such as IMD 34 to operate to collect data for determination of diagnostically relevant metrics that indicative of a need for continued delivery of demand cardiac pacing to the heart of patient 14, and may also facilitate presentation of those metrics in a manner that allows clinicians to make informed decisions about the continued need of a patient for a pacemaker, improving the functioning of cardiovascular devices.

There are a number of situations in which it is expected that a patient may only need a pacemaker temporarily, e.g., for a matter of weeks or months, as opposed to years or for life as is the case for many patients. An example of such a situation is a period of time after a patient has cardiac surgery, such as a minimally invasive transcatheter aortic valve replacement (TAVR) or other procedure, during which some patients develop temporary heart block or other conduction disturbances. In these cases, conduction disturbances may be permanent or temporary. Currently, many of these patients receive permanent pacemakers, although some research indicates that the conduction pathways of such patients recover after days to months.

Consequently, some of these patients may be implanted with a temporary pacemaker. In some examples, IMD 34 may be configured as a temporary cardiac pacemaker. Relative to a permanent pacemaker, a temporary pacemaker may be constructed using materials intended to be implanted within a patient for a shorter period of time, and may include a smaller energy storage capacity.

However, some clinicians may be reluctant to discontinue use of a temporary pacemaker, or even use a temporary pacemaker instead of a permanent pacemaker, due to concerns about continuing heart block or conduction abnormalities. Some clinicians may also be concerned about the ability to detect continuing heart block or conduction abnormalities during a follow up visit. The techniques disclosed herein may enable collection outside of the clinic of metrics that are indicative of a need for continued delivery of demand cardiac pacing and presentation of such metrics to the clinician.

Figure 2:
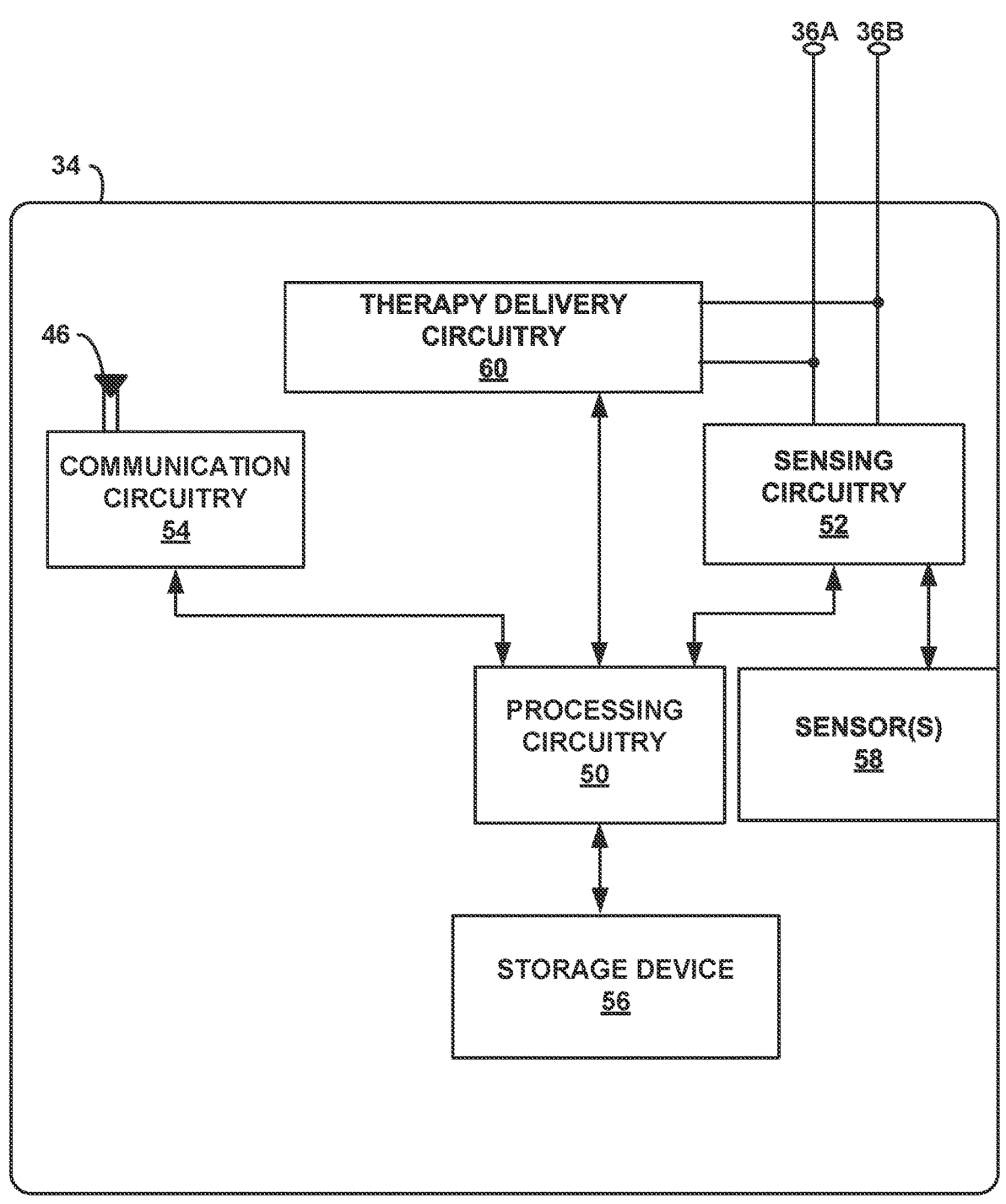
FIG. 2 is a block diagram illustrating an example of the implantable medical device of FIG. 1.

FIG. 2 is a functional block diagram illustrating an example configuration of IMD 34 of FIG. 1 in accordance with one or more techniques described herein. In the illustrated example, IMD 34 includes electrodes 36A and 36B (collectively, "electrodes 36"), antenna 46, processing circuitry 50, sensing circuitry 52, communication circuitry 54, storage device 56, therapy delivery circuitry 60, sensor(s) 58, and power source 91. Although illustrated in FIGS. 1 and 2 as being coupled to two electrodes 36, IMD 34 may be coupled to more than two electrodes in some examples, and the electrodes may be located on one or more leads and/or a housing of IMD 34.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware, or any combination thereof.

Sensing circuitry 52 may be selectively coupled to electrodes 36 in order to sense cardiac signals from heart 12. Sensing circuitry 52 may sense signals from electrodes 36, e.g., to produce a cardiac EGM or subcutaneous electrocardiogram (ECG), in order to facilitate monitoring electrical activity of the heart. In some examples, sensing circuitry 52 may receive signals from sensor(s) 58, which may include one or more temperature sensors, accelerometers, pressure sensors, and/or optical sensors, as examples. For example, sensor(s) 58 may include accelerometers configured to sense atrial contractions. Such accelerometers may be located on lead 18, another lead, or within a housing of IMD 34. In some examples, sensing circuitry 52 may include one or more filters and amplifiers for filtering and amplifying signals received from electrodes 36 and/or sensor(s) 58.

Sensing circuitry 52 may be configured to detect cardiac events attendant to the depolarization of myocardial tissue, e.g., P-waves and R-waves, based on the cardiac electrical signals. In some examples, sensing circuitry 52 detects a cardiac event when the cardiac electrical signal crosses a sensing threshold. The cardiac event detection circuitry may include a rectifier, filter and/or amplifier, a sense amplifier, comparator, and/or analog-to-digital converter.

Sensing circuitry 52 may output indications to processing circuitry 50 in response to sensing of a cardiac event, e.g., detected P-waves or R-waves. In this manner, processing circuitry 50 may receive detected cardiac event signals corresponding to the occurrence of detected R-waves and P-waves. Indications of detected R-waves and P-waves may be used for determining heart rate, detecting arrhythmia episodes and, in the case of demand pacing modes, determining whether an intrinsic cardiac event occurs prior to expiration of an escape interval. Sensing circuitry 52 may also pass one or more digitized EGM signals to processing circuitry 50 for analysis, e.g., for use in cardiac rhythm discrimination. Heart rates or other indications of R-wave and P-wave timing, as well as digitized EGMs, may be stored in storage device 56.

Processing circuitry 50 may control therapy delivery circuitry 60 to deliver cardiac pacing to heart 12 according to therapy parameters stored in storage device 56. Therapy delivery circuitry 60 is selectively coupled to electrodes 36, and is configured to generate and deliver cardiac pacing to heart 12 via electrodes 36. Therapy delivery circuitry 60 may include charging circuitry, one or more charge storage devices, such as one or more high voltage capacitors and/or one or more low voltage capacitors, and switching circuitry that controls when the capacitor(s) are discharged to electrodes 36. Charging of capacitors to a programmed pulse amplitude and discharging of the capacitors for a programmed pulse width may be performed by therapy delivery circuitry 60 according to control signals received from processing circuitry 50.

Storage device 56 stores intervals, counters, or other data, e.g., pacing interval or escape intervals, used by processing circuitry 50 to control the delivery of pacing pulses by therapy delivery circuitry 60. The intervals and/or counters are, in some examples, used by processing circuitry 50 to control the timing of delivery of pacing pulses relative to an intrinsic or paced event in the same chamber or another chamber of heart 12. For example, processing circuitry 50 may control IMD 34 to operate in various demand pacing modes, such as a VVI mode. In such modes, processing circuitry 50 may control therapy delivery circuitry 60 to deliver a pacing pulse at the end of a pacing interval timed from a previous intrinsic or paced depolarization absent occurrence of an intrinsic depolarization during the pacing interval. The duration of the pacing interval may be changed from a normal or pre-programmed duration for various modes as described herein.

In some examples, processing circuitry 50 may control IMD 34 to operate in one of a plurality of operating modes, such as a normal mode, a suspend mode, and a step-down mode. For example, when IMD 34 operates in the normal mode, processing circuitry 50 may cause therapy delivery circuitry 60 to deliver demand cardiac pacing using a target pacing interval.

In some examples, processing circuitry 50 may control IMD 34 to switch from the normal mode to a suspend mode. When IMD 34 operates in the suspend mode, processing circuitry 50 may cause therapy delivery circuitry 60 to suspend the demand cardiac pacing for a time period and resume the demand cardiac pacing using the target pacing interval. In some examples, processing circuitry 50 may "suspend" demand cardiac pacing by setting the pacing interval for demand cardiac pacing to a level that allows for a cardiac pause or asystole, e.g., of 3, 4, or 5 seconds. Processing circuitry 50 may set the interval to a value equivalent to a pacing rate of 20 beats per minute (bpm), 15 bpm, or 12 bpm, as examples. In some examples, processing circuitry 50 may limit the number of cardiac pauses patient 14 can experience during a period of time. For example, processing circuitry 50 may set the number of cardiac pauses to a value equivalent to 5 cardiac pauses per day.

In some examples, processing circuitry 50 may control IMD 34 to switch from a normal mode to a step-down mode. When IMD 34 operates in the step-down mode, processing circuitry 50 may cause therapy delivery circuitry 60 to deliver step-down cardiac pacing using a step-down pacing interval for a time period and resume the demand cardiac pacing using the target pacing interval. The step-down pacing interval may be equivalent to a pacing rate that is 5 bpm, 10 bpm, or 20 bpm lower than the target pacing rate, as examples.

Processing circuitry 50 of IMD 34 may collect data during the operation of IMD 34 in the normal, suspend, and step-down modes, which processing circuitry 50 and/or processing circuitry of another device, such as computing device, may use to determine values of one or more metrics that are indicative of the continued need for demand pacing by patient 14. The processing circuitry may determine the metric values on a per time unit basis. In some examples, the processing circuitry determines values of a metric that is associated with a duration of one or more pacing episodes for each time unit of a plurality of time units, a metric that is associated with an amount of the demand cardiac pacing delivered for each time unit of the plurality of time units, and/or a metric that is associated with a heart rate of patient 14 for each time unit of the plurality of time units.

In some examples, processing circuitry 50 may control IMD 34 to enter the suspend and/or step-down modes based on metric values determined based on data collected during the operation of IMD 34 in the normal mode indicating that patient 14 may no longer need demand cardiac pacing. In some examples, processing circuitry 50 may control IMD 34 to enter into the suspend mode when the metric values determined during operation in the normal or step-down modes indicate that patient 14 likely no longer needs pacing. In another example, processing circuitry 50 may control IMD 34 to enter into a suspend mode or a step-down mode based on the one or more metric values being within predefined ranges.

In some examples, processing circuitry 50 may control IMD 34 to alternate between various step-down modes based on metric values determined based on data collected during the operation of IMD 34 during the step-down modes. For example, based on data collected during the operation of IMD 34 during a fixed step-down mode, processing circuitry 50 may determine the intrinsic heart rhythm of patient 14 is greater than 40 bpm and may control IMD 34 to enter a ramp down scheme with adaptive step-down pacing intervals be equivalent to pacing rates that are 50 bpm, 40 bpm, and 30 bpm. As another example, based on data collected during the operation of 1 MB 34 in the fixed step down, processing circuitry 50 may determine the intrinsic heart rhythm of patient 14 is less than 40 bpm and may control IMD 34 to enter a ramp down scheme with adaptive step-down pacing intervals be equivalent to pacing rates that are 50 bpm, 40 bpm, 50 bpm, 45 bpm, and 40 bpm. Alternating between various step-down modes based on data collected from patient 14 (e.g., intrinsic heart rhythm, accelerometer data) may allow IMD 34 to minimize the time paced at an insufficient rate.

In some examples, processing circuitry 50 may further determine to exit a step-down mode based on various data collected by 1 MB 34. For example, processing circuitry 50 may detect a fall event based on accelerometer data collected by 1 MB 34 and may determine to exit the step-down mode based on detected fall event. As another example, processing circuitry 50 may detect symptoms related to inadequate heart pumping, suspected ectopy, or other problems based on data collected by IMD 34 and may exit the step-down based on the detection.

In some examples, processing circuitry 50 may control IMD 34 to enter into a suspend mode and/or a step-down mode on a periodic basis, such as on an hourly basis, daily basis, or the like, and/or according to a programmed schedule. In one example, processing circuitry 50 may control IMD 34 to enter into a suspend mode and/or a step-down mode during a particular portion of a day. As an example, processing circuitry 50 may control IMD 34 to enter into a suspend mode every two hours for a predetermined number of hours, such as between noon and 5 μm. In some examples, processing circuitry 50 may control 1 MB 34 to enter into a suspend and/or a step-down mode on an adaptive or progressive basis. For example, processing circuitry 50 may extend the step-down reentry time based on determining patient 14 spends less than a certain period of time in the step-down mode. As an example, processing circuitry 50 may extend the step-down reentry time from one hour to two hours based on determining patient 14 spends less than 10 minutes in the step-down mode.

Communication circuitry 54 may include any suitable hardware, firmware, software or any combination thereof for communicating with another device, such as computing device 24, another networked computing device, or another IMD or sensor. Under the control of processing circuitry 50, communication circuitry 54 may receive downlink telemetry from, as well as send uplink telemetry computing device 24 or another device with the aid of an internal or external antenna, e.g., antenna 46. In addition, processing circuitry 50 may communicate with a networked computing device via an external device (e.g., computing device 24) and a computer network, such as the Medtronic CareLink® Network. Antenna 46 and communication circuitry 54 may be configured to transmit and/or receive signals via inductive coupling, electromagnetic coupling, near-field communications, RF communication, Bluetooth®, WI-FI™, or other proprietary or non-proprietary wireless communication schemes. For example, processing circuitry 50 may provide data to be uplinked to computing device 24 via communication circuitry 54 and control signals using an address/data bus. In some examples, communication circuitry 54 may provide received data to processing circuitry 50 via a multiplexer.

In some examples, processing circuitry 50 may send heart rate and pacing data for time units to computing device 24 via communication circuitry 54, and processing circuitry of computing device 24 may determine metric values for the time units. In some examples, IMD 34 may send computing device 24 a plurality of metric values of a plurality of time units, which are then analyzed by computing device 24 and, in some examples, presented to a user in graphical form.

In some examples, storage device 56 includes computer-readable instructions that, when executed by processing circuitry 50, cause IMD 34 and processing circuitry 50 to perform various functions attributed to IMD 34 and processing circuitry 50 herein. Storage device 56 may include any volatile, non-volatile, magnetic, optical, or electrical media. For example, storage device 56 may include random access memory (RAM), read-only memory (ROM), non-volatile RAM (NVRAM), electrically-erasable programmable ROM (EEPROM), erasable programmable ROM (EPROM), flash memory, or any other digital media. Storage device 56 may store, as examples, programmed values for one or more operational parameters of IMD 34 and/or data collected by IMD 34 for transmission to another device using communication circuitry 54. Data stored by storage device 56 and transmitted by communication circuitry 54 to one or more other devices may include pacing and heart rate data for a plurality of time units or values of a plurality of metrics for a plurality of time units.

Figure 3:
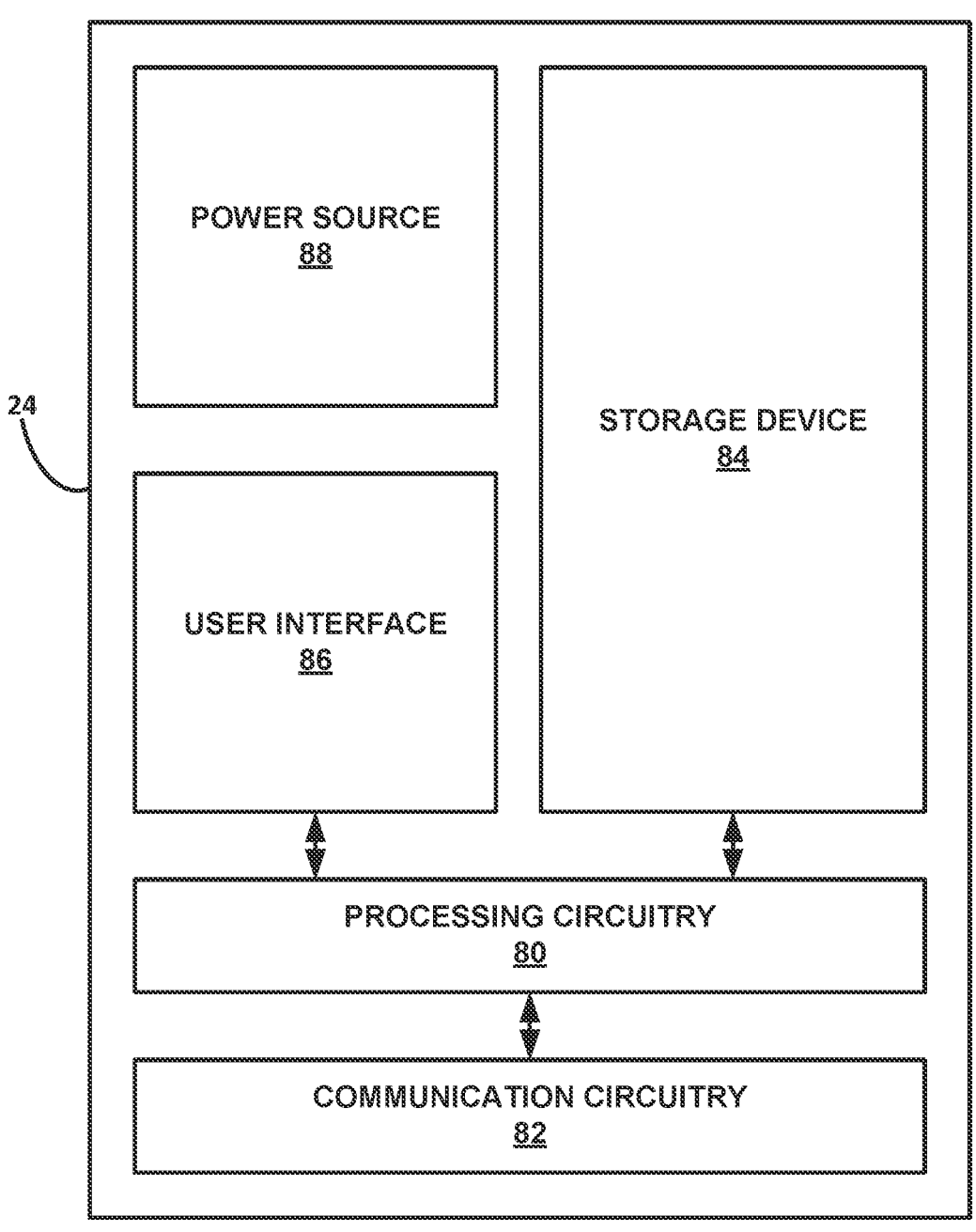
FIG. 3 is a block diagram illustrating an example configuration of the external computing device of FIG. 1.

FIG. 3 is a block diagram illustrating an example configuration of components of computing device 24, in accordance with one or more techniques of this disclosure. In the example of FIG. 3, computing device 24 includes processing circuitry 80, communication circuitry 82, storage device 84, a user interface 86, and power source 88.

Processing circuitry 80 may include one or more processors that are configured to implement functionality and/or process instructions for execution within computing device 24. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 34. Under the control of processing circuitry 80, communication circuitry 82 may receive downlink telemetry from, as well as send uplink telemetry to, IMD 34, or another device. Communication circuitry 82 may be configured to transmit or receive signals via inductive coupling, electromagnetic coupling, Near Field Communication (NFC), RF communication, Bluetooth®, WI-FI™, or other proprietary or non-proprietary wireless communication schemes. Communication circuitry 82 may also be configured to communicate with devices other than IMD 34 via any of a variety of forms of wireless communication and/or network protocols.

Storage device 84 may be configured to store information within computing device 24 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on computing device 24 to temporarily store information during program execution. Storage device 84 may also store a plurality of metrics of a plurality of time units and/or data used to determine the plurality of metrics of the plurality of time units received from IMD 34, as well as a graphical representation of the metric values for the plurality of time units.

Data exchanged between computing device 24 and IMD 34 may include operational parameters. Computing device 24 may transmit data including computer readable instructions which, when implemented by IMD 34, may control IMD 34 to change one or more operational parameters and/or export collected data. For example, processing circuitry 80 may transmit an instruction to IMD 34, which requests IMD 34 to export collected data (e.g., data corresponding to one or both of a heart rate and pacing episodes) to computing device 24. In turn, computing device 24 may receive the collected data from IMD 34 and store the collected data in storage device 84. Additionally, or alternatively, processing circuitry 80 may export instructions to IMD 34 requesting IMD 34 to update demand cardiac pacing parameters, sensing parameters, and/or a schedule for entering suspend and/or step-down modes.

A user, such as a clinician or patient 14, may interact with computing device 24 through user interface 86. User interface 86 includes a display (not shown), such as a liquid crystal display (LCD) or a light emitting diode (LED) display or other type of screen, with which processing circuitry 80 may present information related to IMD 34 (e.g., a plurality of metrics of a plurality of time units and/or a graphical representation of the plurality of metrics of the plurality of time units). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of computing device 24 and provide input. In other examples, user interface 86 also includes audio circuitry for providing audible notifications, instructions or other sounds to the user, receiving voice commands from the user, or both.

Power source 88 is configured to deliver operating power to the components of computing device 24. Power source 88 may include a battery and a power generation circuit to produce the operating power. In some examples, the battery is rechargeable to allow extended operation to convert this into a longer-term temporary or even permanent IMD. Recharging may be accomplished by electrically coupling power source 88 to a cradle or plug that is connected to an alternating current (AC) outlet. In addition, recharging may be accomplished through proximal inductive interaction between an external charger and an inductive charging coil within computing device 24. In other examples, traditional batteries (e.g., nickel cadmium or lithium ion batteries) may be used. In addition, computing device 24 may be directly coupled to an alternating current outlet to operate.

Figure 4:
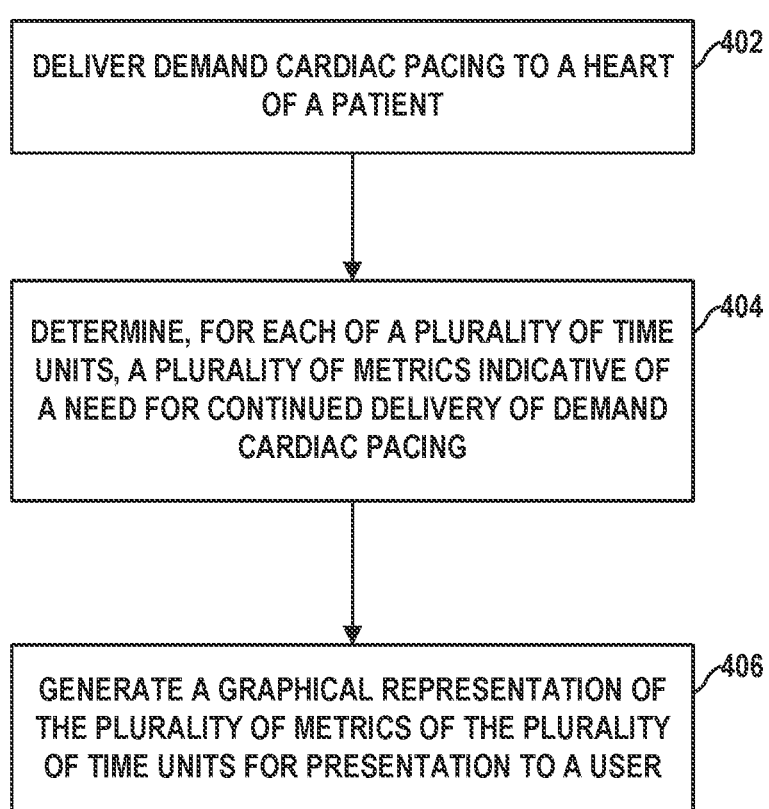
FIG. 4 is a flowchart illustrating an example operation of a medical device system in accordance with the techniques of the disclosure.

FIG. 4 is a flow diagram illustrating an example operation for assessing pacemaker dependency after pacemaker implantation, in accordance with one or more techniques of this disclosure. FIG. 4 is described with respect to IMD 34, computing device 24, and processing circuitry 50 of FIGS. 1-2. However, the techniques of FIG. 4 may be performed by different components of IMD 34, computing device 24, and processing circuitry 50 or by additional or alternative medical device systems. Operations in the flow diagrams described as being performed by processing circuitry 50 of IMD 34 may additionally or alternatively be performed by processing circuitry separated from IMD 34 and/or processing circuitry 80 of computing device 24. In general, the techniques of this disclosure may be performed by processing circuitry of one or more devices of a system, such as one or more devices that include sensors that provide signals and deliver cardiac pacing, or processing circuitry of one or more devices that do not include sensors and/or do not deliver cardiac pacing, but nevertheless analyze patient physiological signals and the delivery of pacing to a patient using the techniques described herein. For example, an external and/or remote device (not pictured in FIG. 1) may include at least a portion of the processing circuitry, and the external device may be configured for remote communication with IMD 34 and/computing device 24 via a network.

In some examples, processing circuitry 50 may cause therapy delivery circuitry 60 to deliver demand cardiac pacing to heart 12 of patient 14 (402). Processing circuitry 50 may then determine, for each of a plurality of time units, a plurality of metrics indicative of a need for continued delivery of demand cardiac pacing (404). In some examples, the plurality of metrics of the time unit may include a metric that is associated with a duration of one or more pacing episodes during the time unit, where each of the one or more pacing episodes includes a respective plurality of consecutive cardiac cycles and/or a respective plurality of semi-consecutive cardiac cycles during which the demand cardiac pacing was delivered. In some examples, the plurality of metrics of the time unit may include a metric that is associated with an amount of the demand cardiac pacing delivered during the time unit. In some examples, the plurality of metrics of the time unit may further include a metric that is associated with a heart rate of the patient during the time unit.

In some examples, processing circuitry 50 waits for a post-implant period after implantation of IMD 34 to begin collecting the pacing and heart rate data used to determine the metric values. Waiting for the post-implant period to expire may allow an expected amount of time of pacemaker dependence to pass before checking to see if the patient is no longer pacemaker dependent. In some examples, processing circuitry 50 may collect the data used to determine the metric values by periodically storing heart rate values and recording the date, timestamp, and duration of episodes in which IMD 34 delivered demand pacing. Episode length may be expressed as a time or number of cardiac cycles with associated pacing rate. In some examples, processing circuitry 50 records such information for cardiac episodes having N or more cardiac cycles, where N is an integer of at least 2. In some examples, N is programmable by a user.

In some examples, processing circuitry, e.g., processing circuitry 80 of computing device 24, may generate a graphical representation of the plurality of metrics of the plurality of time units for presentation to a user, such as a physician (406). In some examples, processing circuitry 50 may transmit the plurality of metrics of the plurality of time units to computing device 24 in wireless communication with IMD 34.

Figure 5:
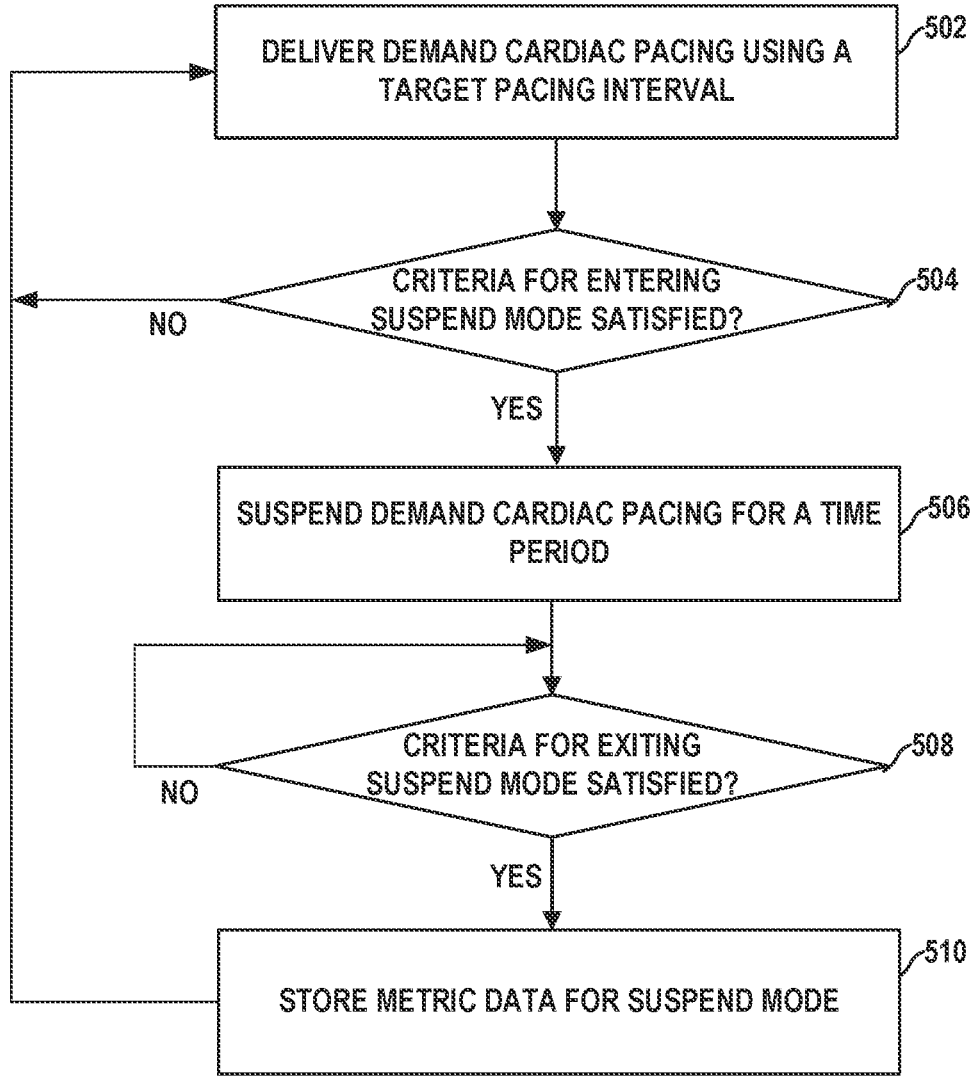
FIG. 5 is a flowchart illustrating an example operation of a medical device in a suspend mode in accordance with the techniques of the disclosure.

FIG. 5 is a flow diagram illustrating an example operation for operating IMD 34 in a suspend mode, in accordance with one or more techniques of this disclosure. FIG. 5 is described with respect to IMD 34, computing device 24, and processing circuitry 50 of FIGS. 1-2. However, the techniques of FIG. 5 may be performed by different components of IMD 34, computing device 24, and processing circuitry 50 or by additional or alternative medical device systems. In some examples, operations illustrated by FIG. 5 may be performed by processing circuitry separated from IMD 34, such as processing circuitry 80 of computing device 24. In general, the techniques of this disclosure may be performed by processing circuitry of one or more devices of a system, such as one or more devices that include sensors that provide signals and deliver cardiac pacing, or processing circuitry of one or more devices that do not include sensors and/or do not deliver cardiac pacing, but nevertheless analyze patient physiological signals and the delivery of pacing to a patient using the techniques described herein. For example, an external and/or remote device (not pictured in FIG. 1) may include at least a portion of the processing circuitry, and the external device may be configured for remote communication with IMD 34 and/computing device 24 via a network.

In some examples, processing circuitry 50 may cause IMD 34 to deliver demand cardiac pacing using a target pacing interval (502). While delivering demand cardiac pacing, processing circuitry 50 may determine whether one or more criteria for entering a suspend mode are satisfied (504). In some examples, processing circuitry 50 waits for a post-implant period after implantation of IMD 34 prior to entering a suspend mode. In some examples, processing circuitry 50 waits for expiration of a timer started from completion of a previous suspend mode before beginning a current suspend mode. Other criteria for starting the suspend mode may include criteria related to relatively low use of demand pacing, an accelerometer reading (e.g., indicating relatively low activity), and heart rate below a threshold, such as 100 bpm. Example criteria related to relatively low use of demand pacing include use of a lower target pacing interval for a threshold amount of time and an amount of recent cardiac cycles that were paced being below a threshold. If the criteria for entering the suspend mode are not satisfied (NO of 504), processing circuitry 50 may continue to deliver demand cardiac pacing (502) and evaluate the criteria (504).

If the criteria for entering the suspend mode are satisfied (YES of 504), processing circuitry 50 may cause therapy delivery circuitry 60 to suspend the demand cardiac pacing for a time period (506). As discussed herein, processing circuitry 50 may cause therapy delivery circuitry 60 to suspend the demand cardiac pacing by increasing a pacing interval during the time period or stopping the pacing entirely for the time period. During the suspend mode, processing circuitry 50 may determine whether one or more criteria for exiting the suspend mode are satisfied (508). The time period may be fixed or may extend until the one or more criteria for exiting the suspend mode are satisfied. Example criteria for exiting the suspend mode include occurrence of a cardiac pause of a threshold length, such as five seconds, or average heart rate less than (or V-V interval greater than) a threshold rate (or interval) over a time period. Other example criteria for exiting the suspend mode include detection of a premature ventricular contraction (PVC) or a sudden fast rate interval, e.g., to minimize the risk of a short-long-short induced arrhythmia. If the criteria for exiting the suspend mode are not satisfied (NO of 508), processing circuitry 50 may continue in the suspend mode and continue to evaluate the criteria.

If the criteria for exiting the suspend mode are satisfied (YES of 508), processing circuitry 50 may store metric data for the suspend mode (510) and cause therapy delivery circuitry 60 to resume the demand cardiac pacing using the target pacing interval (502). Example metric data that may be collected during the suspend mode include the length of the suspend mode from initiation to exit criteria satisfaction, whether a cardiac pause of threshold length occurred, information regarding intrinsic heart rate during the suspend mode, such as an average or other mid-based statistic of heart rate or V-V interval, and an amount (e.g., percentage) of cardiac intervals having a heart rate below (or V-V interval above) a threshold. In some examples, information regarding intrinsic heart rate during the suspend mode may be presented to patient 14 or a third party via a display device, such as computing device.

Figure 6:
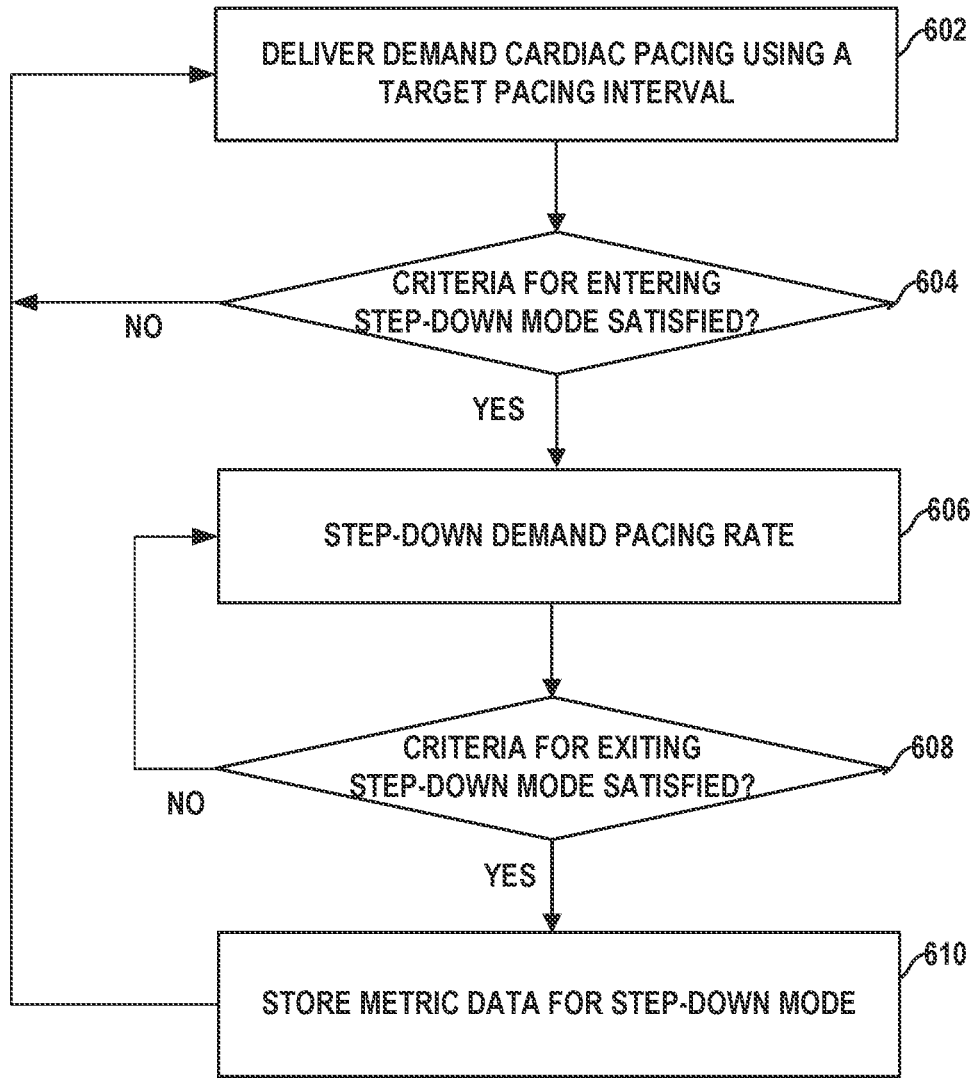
FIG. 6 is a flowchart illustrating an example operation of a medical device in a step-down mode in accordance with the techniques of the disclosure.

FIG. 6 is a flow diagram illustrating an example operation for operating IMD 34 in a step-down mode, in accordance with one or more techniques of this disclosure. FIG. 6 is described with respect to IMD 34, computing device 24, and processing circuitry 50 of FIGS. 1-2. However, the techniques of FIG. 6 may be performed by different components of IMD 34, computing device 24, and processing circuitry 50 or by additional or alternative medical device systems. In some examples, operations illustrated by FIG. 6 may be performed by processing circuitry separated from IMD 34, such as processing circuitry 80 of computing device 24. In general, the techniques of this disclosure may be performed by processing circuitry of one or more devices of a system, such as one or more devices that include sensors that provide signals and deliver cardiac pacing, or processing circuitry of one or more devices that do not include sensors and/or do not deliver cardiac pacing, but nevertheless analyze patient physiological signals and the delivery of pacing to a patient using the techniques described herein. For example, an external and/or remote device (not pictured in FIG. 1) may include at least a portion of the processing circuitry, and the external device may be configured for remote communication with IMD 34 and/computing device 24 via a network.

In some examples, processing circuitry 50 may cause IMD 34 to deliver demand cardiac pacing using a target pacing interval (602). While delivering demand cardiac pacing, processing circuitry 50 may determine whether one or more criteria for entering a step-down mode are satisfied (604). In some examples, processing circuitry 50 waits for a post-implant period after implantation of IMD 34 prior to entering a step-down mode. In some examples, processing circuitry 50 waits for expiration of a timer started from completion of a previous step-down mode before beginning a current step-down mode. Other criteria for starting the step-down mode may include criteria related to relatively low use of demand pacing, such as use of a lower target pacing interval for a threshold amount of time and an amount of recent cardiac cycles that were paced being below a threshold. If the criteria for entering the step-down mode are not satisfied (NO of 604), processing circuitry 50 may continue to deliver demand cardiac pacing (602) and evaluate the criteria (604).

If the criteria for entering the suspend mode are satisfied (YES of 604), processing circuitry 50 may cause therapy delivery circuitry 60 to deliver step-down cardiac pacing using a step-down pacing interval for a time period (606). In some examples, processing circuitry 50 may cause therapy delivery circuitry 60 to deliver demand cardiac pacing at a fixed step-down pacing interval (such as 30 bpm) for the time period. In some examples, processing circuitry 50 may cause therapy delivery circuitry 60 to increase the step-down pacing interval in steps, e.g., by stepping down the pacing rate floor in increments of 5 bpm until a maximum step-down pacing interval (such as an interval associated with a pacing rate of 30 bpm) is reached.

During the step-down mode, processing circuitry 50 may determine whether one or more criteria for exiting the step-down mode are satisfied (608). The time period may be fixed or may extend until the one or more criteria for exiting the step-down mode are satisfied. An example criterion for exiting the step-down mode include occurrence of a threshold number (such as one) of paced cardiac cycles at the step-down pacing interval. If the criteria for exiting the step-down mode are not satisfied (NO of 608), processing circuitry 50 may control therapy delivery circuitry 60 to continue in the step-down mode and continue to evaluate the criteria.

If the criteria for exiting the step-down mode are satisfied (YES of 608), processing circuitry 50 store metric data for the suspend mode (610) and may control therapy delivery circuitry 60 to resume the demand cardiac pacing using the target pacing interval (602). Example metric data that may be collected during the step-down mode include date, time-stamp, and duration of the step-down mode, average or other mid-based statistic of heart rate in the suspend mode, or any other metric described herein. In some examples, metric data collected during the step-down mode may be presented to patient 14 or a third party via a display device, such as computing device 24.

In some examples, metric data collected during diagnostic modes, e.g., the suspend mode discussed in conjunction with FIG. 5 and/or the step-down mode discussed in conjunction with FIG. 6, includes EGM waveform data and/or R-R interval data preceding or leading to exiting the diagnostic mode, e.g., due to low intrinsic rate or pause. Such data may allow a clinician to identify a conduction disturbance underlying the exiting of the diagnostic mode. The identification of the conduction disturbance may be evidence of need for further demand pacing. In some examples, the identification of the conduction disturbance may be evidence of a need for a more permanent IMD, e.g., pacemaker, to treat the patient. For example, as described above, when operating in diagnostic modes, IMD 34 may store data indicative of when intrinsic heart rate drops falls below a low threshold based upon a dropped beat and/or a low escape rate, which may allow a clinician to diagnose atrioventricular block, and distinguish different types of blocks or pauses.

Figure 7A:
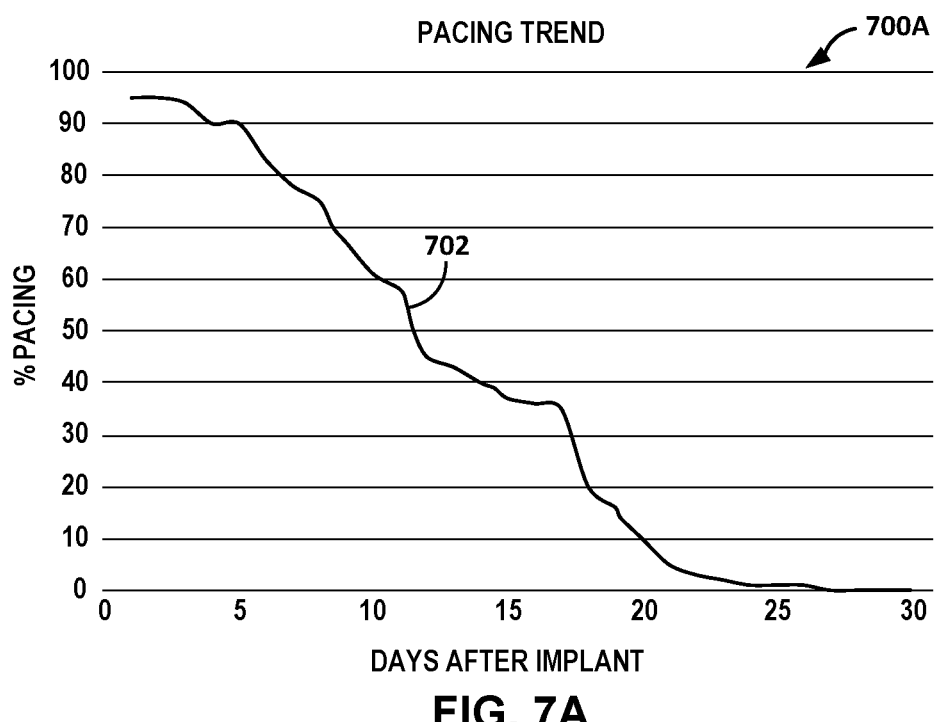
FIGS. 7A and 7B are graphs illustrating an example historical pacing trend and an example heart rate trend generated according to the techniques of this disclosure.
Figure 7B:
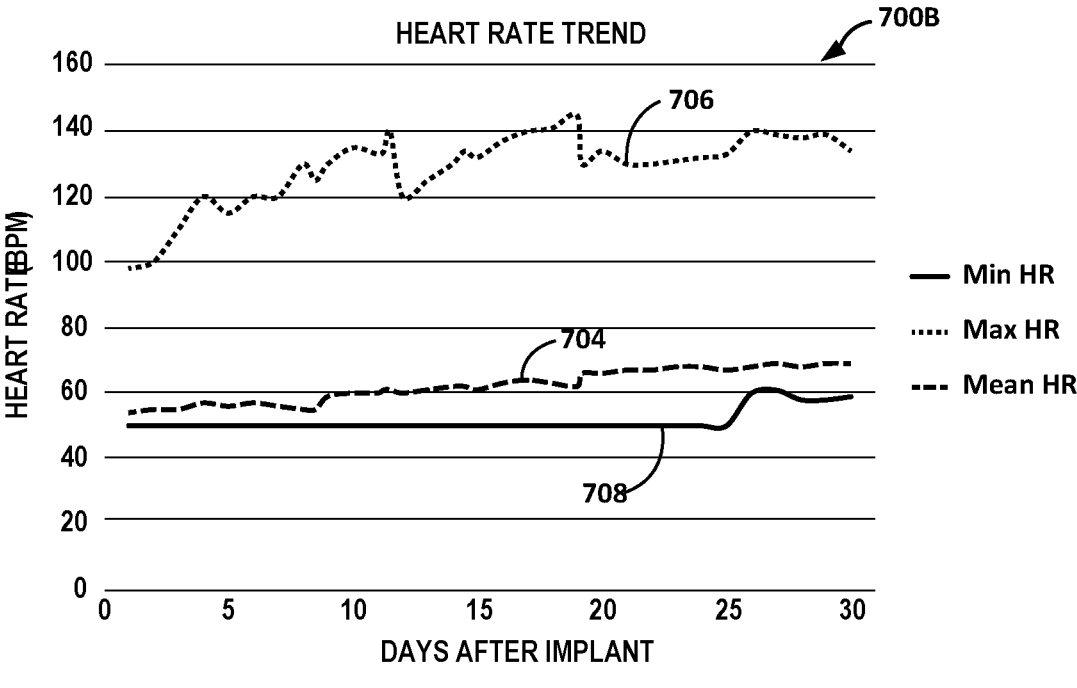

FIGS. 7A and 7B are graphs illustrating an example historical pacing trend and an example heart rate trend generated according to the techniques of this disclosure. Graphs 700A and 700B represent exemplary data outputted by IMD 34 and/or presented by computing device 24. However, it should be understood that other computer devices may be configured to output or present such data. Graph 700A illustrates the pacing percentage 702 provided to a heart of an exemplary patient over a plurality of time units. Graph 700B illustrates the mean heart rate 704, the maximum heart rate 706, and the minimum heart rate 708 of an exemplary patient over a plurality of time units.

Figure 8A:
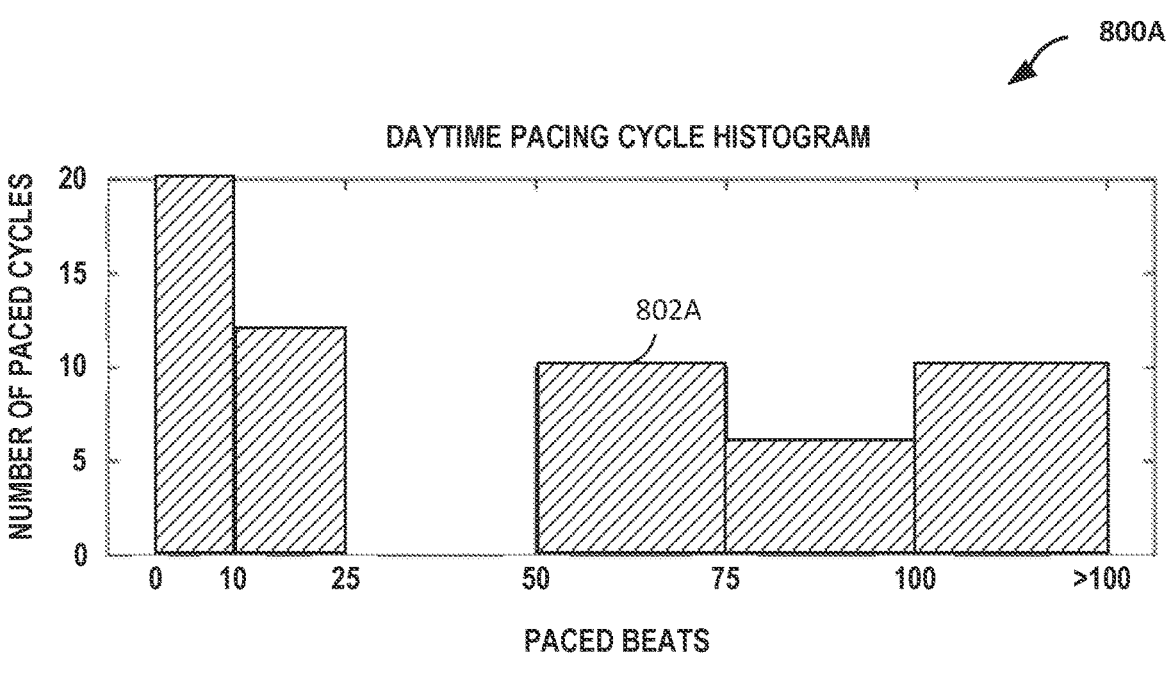
FIGS. 8A and 8B are graphs illustrating an example daytime pacing cycle histogram and a nighttime pacing cycle histogram generated according to the techniques of this disclosure.
Figure 8B:
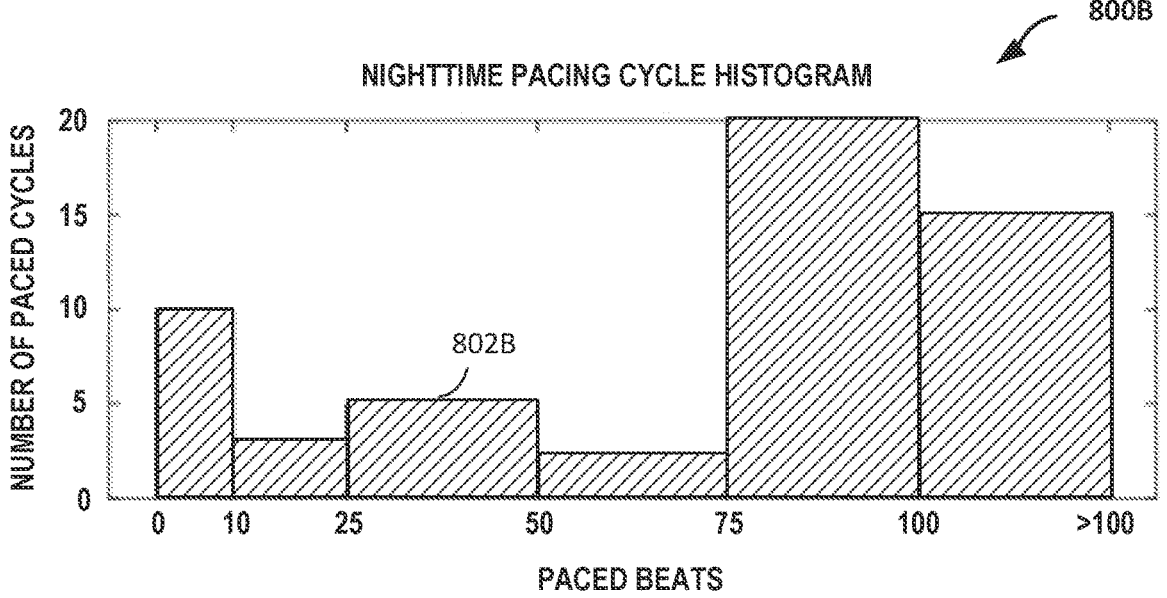

FIGS. 8A and 8B are graphs illustrating an example daytime pacing cycle histogram and a nighttime pacing cycle histogram generated according to the techniques of this disclosure. Graphs 800A and 800B represent exemplary data outputted by IMD 34 and/or presented by computing device 24. However, it should be understood that other computer devices may be configured to output or present such data. Graph 800A illustrates the number of pacing cycles 802A with paced beasts between 0 to 10, 10 to 25, 25 to 50, 50 to 75, 75 to 100, and paced beats greater than 100 in the daytime of an exemplary period. For example, graph 800A shows there are 20 pacing cycles with paced beats between 0 to 10 in the daytime of the exemplary period. Similarly, Graph 800B illustrates the number of pacing cycles 802B with paced beasts between 0 to 10, 10 to 25, 25 to 50, 50 to 75, 75 to 100, and paced beats greater than 100 in the nighttime of an exemplary period. For example, graph 800B shows there are 20 pacing cycles with paced beats between 75 to 100 in the nighttime of the exemplary period. It should be understood that theses ranges could change and are only exemplary.

Figure 9A:
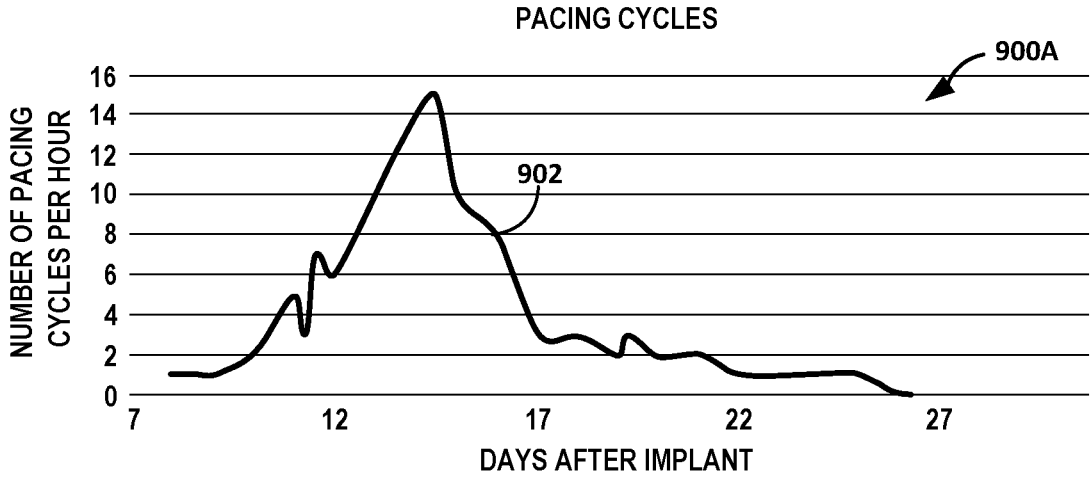
FIGS. 9A and 9B are graphs illustrating example pacing cycle reports generated according to the techniques of this disclosure.
Figure 9B:
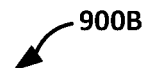

FIGS. 9A and 9B are graphs illustrating example pacing cycle reports generated according to the techniques of this disclosure. Graphs 900A and 900B represent exemplary data outputted by IMD 34 and/or presented by computing device 24. However, it should be understood that other computer devices may be configured to output or present such data. Graph 900A illustrates the number of pacing cycles per hour 902 provided to the heart of an exemplary patient over a plurality of days. Graph 900A illustrates the number of pacing cycles per hour 902 provided to the heart of an exemplary patient over a plurality of days. Graph 900B illustrates pacing record 904 for each pacing episode of a plurality of pacing episodes. For example, graph 900B shows there is a pacing episode start at 3:22 AM on Nov. 12, 2019, and the pacing episode has a during of 14 hours, 07 minutes, and 03 seconds.

Some examples of data collected and metrics indicative of a continued need for demand cardiac pacing have been described herein, and others are contemplated. For example, metrics indicative of a continued need for demand cardiac pacing may include duration of episodes of continuous or near-continuous pacing or intrinsic cardiac activity, or amounts (percentage or fraction) of either over a time period.

In addition to the example techniques for assessing continued need for demand cardiac pacing described herein, medical device systems configured as described herein may be configured to monitor other metrics of the patient's condition and/or continued need for monitoring or therapy, e.g., by a pacemaker or other IMD. For example, systems configured to sense atrial activity as described herein may detect episodes of atrial tachyarrhythmia. Systems not configured to detect atrial activity may also detect atrial fibrillation based on its effect on R-R interval patterns. Additionally, or alternatively, the systems described herein may detect ventricular tachyarrhythmia, which may allow a clinician to determine whether a patient should receive a cardioverter defibrillator.

The techniques described in this disclosure, including those attributed to IMD 34, computing device 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

The following examples are illustrative of the techniques described herein.

Example 1

A system comprising: an implantable medical device (IMD) comprising: sensing circuitry configured to sense, via a plurality of electrodes, cardiac electrical signals of a patient; therapy delivery circuitry configured to deliver demand cardiac pacing to a heart of the patient via the plurality of electrodes based on the cardiac electrical signals; and processing circuitry. The processing circuitry is configured to determine, for each of a plurality of time units, based on the cardiac electrical signals and the delivery of demand cardiac pacing during the time units, a plurality of metrics indicative of a need for continued delivery of demand cardiac pacing to the heart of the patient. The plurality of metrics comprise a metric associated with a duration of one or more pacing episodes during the time unit, each of the one or more pacing episodes comprising a respective plurality of consecutive cardiac cycles during which the demand cardiac pacing was delivered for at least a threshold portion of the cardiac cycles. The processing circuitry is configured to generate a graphical representation of the plurality of metrics of the plurality of time units for presentation to a user.

Example 2

The system of example 1, wherein the metric associated with a duration of one or more pacing episodes during the time unit comprises, for each of the one or more pacing episodes, at least one of a number of the respective plurality of consecutive cardiac cycles or a total time duration of the episode.

Example 3

The system of example 1 or 2, wherein the plurality of metrics further comprises: a metric associated with an amount of the demand cardiac pacing delivered during the time unit.

Example 4

The system of any of examples 1 to 3, wherein the plurality of metrics further comprises: a metric associated with a heart rate of the patient during the time unit.

Example 5

The system of example 4, wherein the heart rate comprises at least one of an average heart rate, a median heart rate, a mode heart rate, a minimum heart rate, a low-percentile heart rate, a maximum heart rate, or a high-percentile heart rate during the time unit.

Example 6

The system of any of example 1 to 5, wherein the processing circuitry is configured to: cause the IMD to operate in a diagnostic mode for a time period; and collect at least one of the plurality of metrics during the time period.

Example 7

The system of example 6, wherein the plurality of metrics further comprises a metric comprising a diagnostic mode event log.

Example 8

The system of example 6 or 7, wherein the plurality of metrics further comprises a metric associated with a length of the time period.

Example 9

The system of any of examples 6 to 8, wherein the diagnostic mode comprises a suspend mode, wherein the suspend mode is a mode of operation in which the therapy delivery circuitry is configured to: suspend the demand cardiac pacing for a time period; and collect at least one of the plurality of metrics during the time period.

Example 10

The system of any of examples 6 to 9, wherein the diagnostic mode comprises a step-down mode, wherein the step-down mode is a mode of operation in which the therapy delivery circuitry is configured to: deliver step-down cardiac pacing using one or more step-down pacing intervals for a time period; and collect at least one of the plurality of metrics during the time period.

Example 11

The system of any of examples 1 to 10, wherein the processing circuitry comprises processing circuitry of an external computing device in wireless communication with the IMD.

Example 12

The system of any of examples 1 to 11, wherein the processing circuitry comprises processing circuitry of the IMD.

Example 13

A method comprising: sensing, via a plurality of electrodes of an implantable medical device (IMD), cardiac electrical signals of a patient; delivering demand cardiac pacing to a heart of the patient via the plurality of electrodes based on the cardiac electrical signals; determining, for each of a plurality of time units, based on the cardiac electrical signals and the delivery of demand cardiac pacing during the time units, a plurality of metrics indicative of a need for continued delivery of demand cardiac pacing to the heart of the patient, wherein the plurality of metrics comprise: a metric associated with a duration of one or more pacing episodes during the time unit, each of the pacing episodes comprising a respective plurality of consecutive cardiac cycles during which the demand cardiac pacing was delivered for at least a threshold portion of the cardiac cycles; and generating a graphical representation of the plurality of metrics of the plurality of time units for presentation to a user.

Example 14

The method of example 13, wherein the metric associated with a duration of one or more pacing episodes during the time unit comprises, for each of the one or more pacing episodes, at least one of a number of the respective plurality of consecutive cardiac cycles or a total time duration of the episode.

Example 15

The method of example 13 or 14, wherein the plurality of metrics further comprises: a metric associated with an amount of the demand cardiac pacing delivered during the time unit.

Example 16

The method of any of examples 13 to 15, wherein the plurality of metrics further comprises: a metric associated with a heart rate of the patient during the time unit.

Example 17

The method of example 16, wherein the heart rate comprises at least one of an average heart rate, a median heart rate, a mode heart rate, a minimum heart rate, a low-percentile heart rate, a maximum heart rate, or a high-percentile heart rate during the time unit.

Example 18

The method of any of examples 13 to 17, further comprises: causing the IMD to operate in a diagnostic mode for a time period; and collecting at least one of the plurality of metrics during the time period.

Example 19

The method of example 18, wherein the plurality of metrics further comprises a metric comprising a diagnostic mode event log.

Example 20

The method of example 18 or 19, wherein the plurality of metrics further comprises a metric associated with a length of the time period.

Example 21

The method of any of examples 18 to 20, wherein the diagnostic mode comprises a suspend mode, wherein the suspend mode is a mode of operation in which the therapy delivery circuitry is configured to: suspend the demand cardiac pacing for a time period; and collect at least one of the plurality of metrics during the time period.

Example 22

The method of any of examples 18 to 21, wherein the diagnostic mode comprises a step-down mode, wherein the step-down mode is a mode of operation in which the therapy delivery circuitry is configured to: deliver step-down cardiac pacing using a step-down pacing interval for a time period; and collect at least one of the plurality of metrics during the time period.

Example 23

The method of any of examples 18 to 22, further comprises: transmitting the plurality of metrics to an external computing device in wireless communication with the IMD.

Example 24

A non-transitory computer-readable storage medium comprising program instructions that, when executed by processing circuitry of a medical system, cause the processing circuitry to perform the method of any of examples 13 to 23.

Various examples have been described. These and other examples are within the scope of the following claims.

What is claimed is:

1. A system comprising:
an implantable medical device (IMD) comprising:
a plurality of electrodes;
sensing circuitry configured to sense, via the plurality of electrodes, cardiac electrical signals of a patient;
therapy delivery circuitry configured to deliver demand cardiac pacing to a heart of the patient via the plurality of electrodes based on the cardiac electrical signals; and processing circuitry configured to:
determine, for each time unit of a plurality of time units, based on the cardiac electrical signals and the delivery of demand cardiac pacing during the time units, a plurality of metrics indicative of a need for continued delivery of demand cardiac pacing to the heart of the patient, wherein the plurality of metrics comprise:
a metric based on a duration of one or more pacing episodes during the time unit, each of the one or more pacing episodes comprising a respective plurality of consecutive cardiac cycles during which the demand cardiac pacing was delivered for at least a pre-determined threshold portion of the cardiac cycles, wherein the processing circuitry is configured to identify the one or more pacing episodes by at least, for each plurality of the respective pluralities of consecutive cardiac cycles, determining that a respective portion of the consecutive cardiac cycles during which demand cardiac pacing was delivered satisfies the pre-determined threshold portion; and
generate a graphical representation of the plurality of metrics of the plurality of time units for presentation to a user,
wherein the metric based on a duration of one or more pacing episodes during the time unit comprises, for each of the one or more identified pacing episodes, at least one of a number of the respective plurality of consecutive cardiac cycles or a total time duration of the pacing episode.

2. The system of claim 1, wherein the metric based on a duration of one or more pacing episodes during the time unit comprises, for each of the one or more pacing episodes the number of the respective plurality of consecutive cardiac cycles.

3. The system of claim 1, wherein the plurality of metrics further comprises:
a metric associated with an amount of the demand cardiac pacing delivered during the time unit.

4. The system of claim 1, wherein the plurality of metrics further comprises:
a metric associated with a heart rate of the patient during the time unit.

5. The system of claim 4, wherein the metric associated with heart rate comprises at least one of an average heart rate, a median heart rate, a mode heart rate, a minimum heart rate, a low-percentile heart rate, a maximum heart rate, or a high-percentile heart rate during the time unit.

6. The system of claim 1, wherein the processing circuitry is configured to:
cause the IMD to operate in a diagnostic mode for a time period; and
collect at least one metric of the plurality of metrics during the time period.

7. The system of claim 6, wherein the plurality of metrics further comprises a metric comprising a diagnostic mode event log.

8. The system of claim 6, wherein the plurality of metrics further comprises a metric associated with a length of the time period.

9. The system of claim 6, wherein the diagnostic mode comprises a suspend mode, wherein the suspend mode is a mode of operation in which the therapy delivery circuitry is configured to suspend the demand cardiac pacing for the time period, and the processing circuitry is configured to collect at least one metric of the plurality of metrics during the time period.

10. The system of claim 6, wherein the diagnostic mode comprises a step-down mode, wherein the step-down mode is a mode of operation in which the therapy delivery circuitry is configured to deliver step-down cardiac pacing using one or more step-down pacing intervals for the time period.

11. The system of claim 1, wherein the processing circuitry comprises processing circuitry of an external computing device in wireless communication with the IMD.

12. The system of claim 1, wherein the processing circuitry comprises processing circuitry of the IMD.

13. A method comprising:

sensing, via a plurality of electrodes of an implantable medical device (IMD), cardiac electrical signals of a patient;

delivering, by the IMD, demand cardiac pacing to a heart of the patient via the plurality of electrodes based on the cardiac electrical signals;

determining, for each time unit of a plurality of time units, based on the cardiac electrical signals and the delivery of demand cardiac pacing during the time units, a plurality of metrics indicative of a need for continued delivery of demand cardiac pacing to the heart of the patient, wherein the plurality of metrics comprise:

a metric based on a duration of one or more pacing episodes during the time unit, each of the pacing episodes comprising a respective plurality of consecutive cardiac cycles during which the demand cardiac pacing was delivered for at least a predetermined threshold portion of the cardiac cycles, wherein the method further comprises identifying the one or more pacing episodes by at least, for each plurality of the respective pluralities of consecutive cardiac cycles, determining that a respective portion of the consecutive cardiac cycles during which demand cardiac pacing was delivered satisfies the pre-determined threshold portion; and generating a graphical representation of the plurality of metrics of the plurality of time units for presentation to a user, wherein the metric based on a duration of one or more pacing episodes during the time unit comprises, for each of the one or more identified pacing episodes, at least one of a number of the respective plurality of consecutive cardiac cycles or a total time duration of the pacing episode.

14. The method of claim 13, wherein the metric based on a duration of one or more pacing episodes during the time unit comprises the number of the respective plurality of consecutive cardiac cycles.

15. The method of claim 13, wherein the plurality of metrics further comprises:

a metric associated with an amount of the demand cardiac pacing delivered during the time unit.

16. The method of claim 13, wherein the plurality of metrics further comprises:

a metric associated with a heart rate of the patient during the time unit.

17. The method of claim 16, wherein the metric associated with heart rate comprises at least one of an average heart rate, a median heart rate, a mode heart rate, a minimum heart rate, a low-percentile heart rate, a maximum heart rate, or a high-percentile heart rate during the time unit.

18. The method of claim 13, further comprising:

causing the IMD to operate in a diagnostic mode for a time period; and collecting at least one metric of the plurality of metrics during the time period.

19. The method of claim 18, wherein the plurality of metrics further comprises a metric comprising a diagnostic mode event log.

20. The method of claim 18, wherein the plurality of metrics further comprises a metric associated with a length of the time period.

21. The method of claim 18, wherein the diagnostic mode comprises a suspend mode, wherein the suspend mode is a mode of operation in which the IMD is configured to suspend the demand cardiac pacing for the time period, wherein determining the plurality of metrics comprises collecting at least one of the plurality of metrics during the time period.

22. The method of claim 18, wherein the diagnostic mode comprises a step-down mode, wherein the step-down mode is a mode of operation in which the IMD is configured to deliver step-down cardiac pacing using a step-down pacing interval for a time period.

23. The method of claim 18, further comprising:

transmitting the plurality of metrics to an external computing device in wireless communication with the IMD.

24. A non-transitory computer-readable storage medium comprising program instructions that, when executed by processing circuitry of a medical system, cause the processing circuitry to:

receive cardiac electrical signals of a patient sensed via a plurality of electrodes of an implantable medical device (IMD);

control the IMD to deliver demand cardiac pacing to a heart of the patient via the plurality of electrodes based on the cardiac electrical signals;

determine, for each time unit of a plurality of time units, based on the cardiac electrical signals and the delivery of demand cardiac pacing during the time units, a plurality of metrics indicative of a need for continued delivery of demand cardiac pacing to the heart of the patient, wherein the plurality of metrics comprise:

a metric based on a duration of one or more pacing episodes during the time unit, each of the pacing episodes comprising a respective plurality of consecutive cardiac cycles during which the demand cardiac pacing was delivered for at least a predetermined threshold portion of the cardiac cycles, wherein the processing circuitry is to identify the one or more pacing episodes by at least, for each plurality of the respective pluralities of consecutive cardiac cycles, determining that a respective portion of the consecutive cardiac cycles during which demand cardiac pacing was delivered satisfies the pre-determined threshold portion; and generate a graphical representation of the plurality of metrics of the plurality of time units for presentation to a user, wherein the metric based on a duration of one or more pacing episodes during the time unit comprises, for each of the one or more identified pacing episodes, at least one of a number of the respective plurality of consecutive cardiac cycles or a total time duration of the pacing episode.

* * * * *